United States Patent [19]

Coulombe

[11] Patent Number: 4,844,249
[45] Date of Patent: Jul. 4, 1989

[54] MEDICAL SUPPLIES CONTAINER

[76] Inventor: Maurice Coulombe, 4296 Place Charles, Bédard Charlesbourg, Canada, G1H 5L9

[21] Appl. No.: 201,917

[22] Filed: Jun. 3, 1988

[51] Int. Cl.⁴ .............................................. A61B 17/06
[52] U.S. Cl. .................................... 206/438; 206/365
[58] Field of Search ....................... 206/365, 366, 438

[56] References Cited

U.S. PATENT DOCUMENTS 2,659,485 11/1953 Dudley et al. ........................ 206/365
4,643,303 2/1987 Arp et al. ........................ 206/438 X
4,742,910 5/1988 Staebler ................................ 206/365

Primary Examiner—Allen M. Ostrager

[57] ABSTRACT

A medical supplies container comprising a base wall, four upright side walls and a peripheral flange projecting outwardly from the top edges of the side walls. The flange and the side walls have a few bores each freely engageably by a hypodermic syringe having a rigid body part, a needle and a needle holder freely engageable into the flange bore. Each side wall bore registers with a given flange bore. Each bore or pair of registering bores define a boring axis and the bores are of such a shape that, when the needle holder is engaged in a bore or in a pair of registering bores, and when the syringe member rigid body part is biased slightly transversely of the boring axis, any pulling of the rigid body part allows egress of the syringe and associated needle exclusively of the needle holder, wherein the syringe needle can be removed from the holder thereof single-handedly without having to grasp the holder. Thereafter, when the syringe has been used to withdraw blood from a patient and to transfer it to a suitable vial, the syringe needle can be snappingly reinserted into its holder without having to manually support the latter. Finally, by pulling the syringe along its boring axis, the needle holder is brought therewith without having to manually pull the latter therewith.

11 Claims, 2 Drawing Sheets

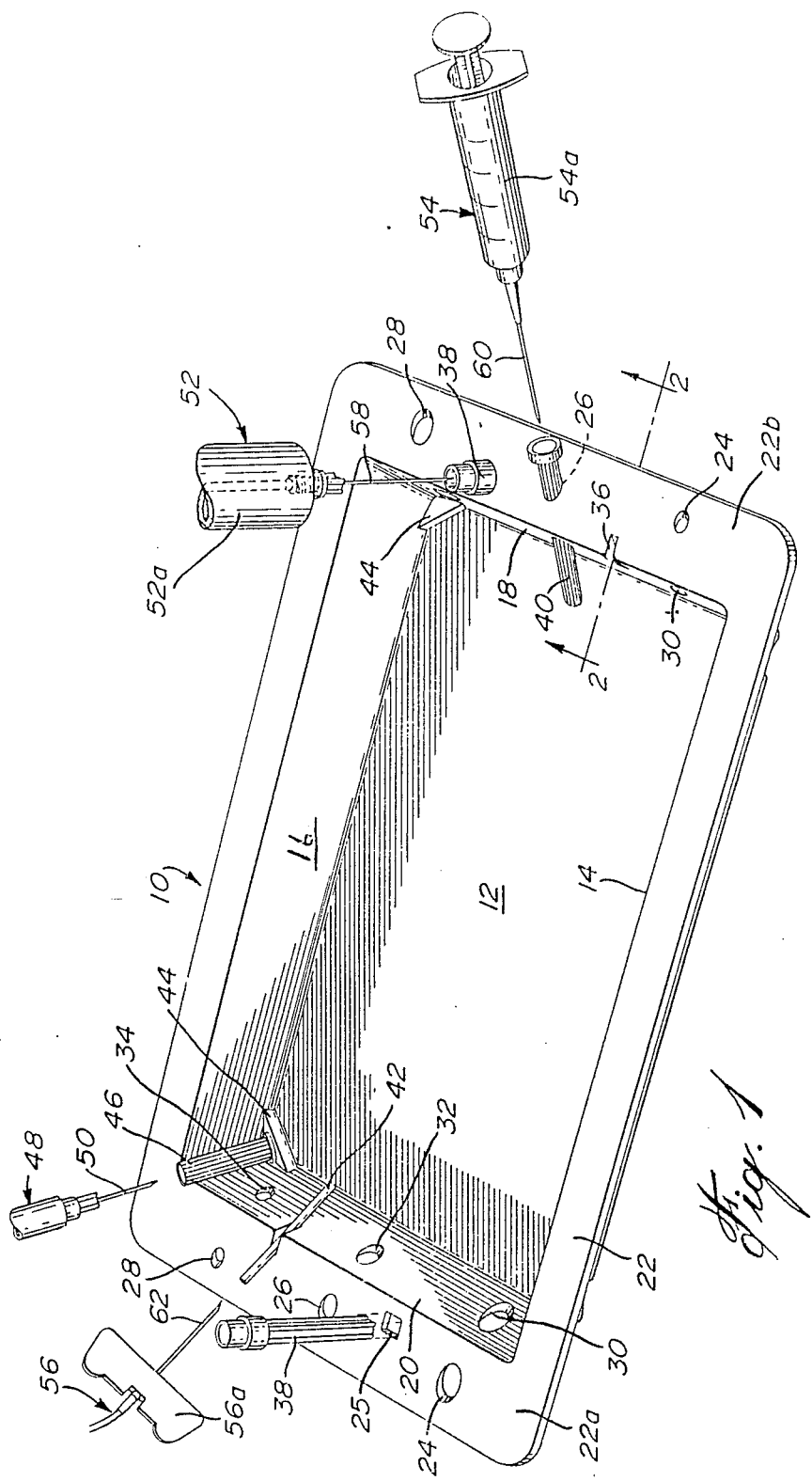

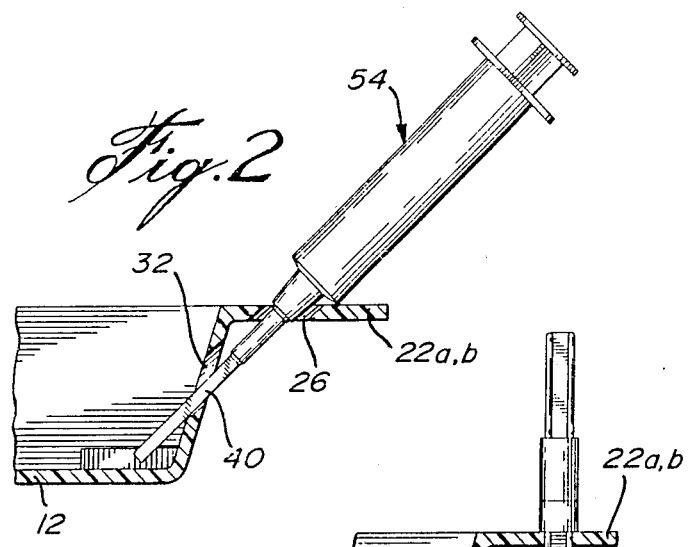
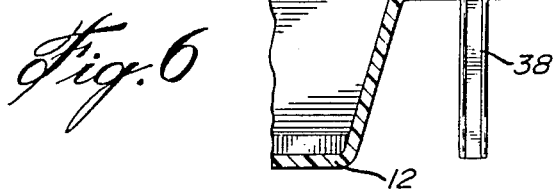
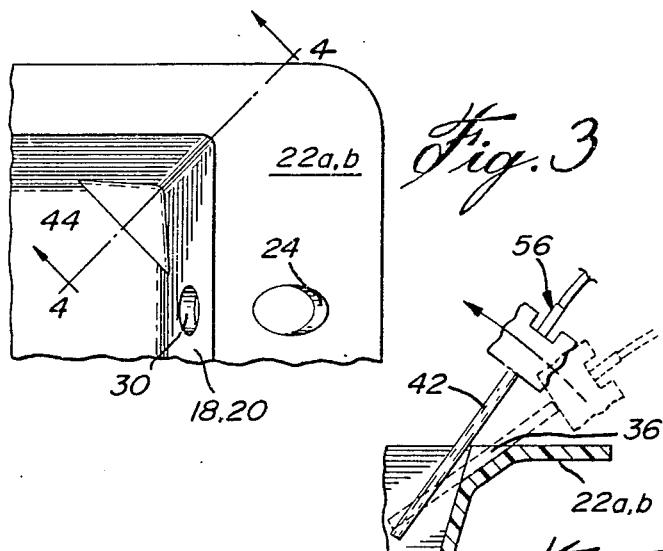
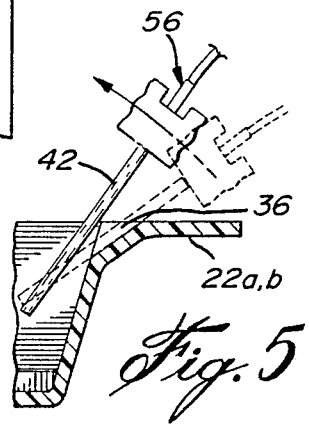
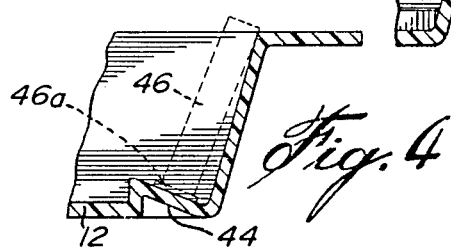

MEDICAL SUPPLIES CONTAINER

FIELD OF THE INVENTION

This invention relates to the field of medical equipment, especially the equipment for paramedical staff.

BACKGROUND OF THE INVENTION

There is considerable concern in the industrial world nowadays in ways to prevent the spread of a most dangerous disease called "Auto Immune Deficiency Syndrome" or AIDS. AIDS was first detected in the African continent in the years 1978-1979, and has now spread to the five continent and is now claiming many casualties worldwide. As is now well known, this disease is caused by a virus which proliferates in blood or sperm, so as to infect primates (including man) through either blood contamination or during sexual intercourse. It is believed by the scientific community that the first human AIDS carrier was contamined in Central Africa by the blood of an AIDS-infected chimpanzee during tribal initiation rites involving the "exchange" of blood between the animal and humans.

OBJECTS OF THE INVENTION

The main goal of the invention is to prevent the spread of a most dangerous disease called "Auto Immune Deficiency Syndrome" or AIDS.

A corollary object of the invention is to facilitate the work of paramedical staff, in particular nurses.

SUMMARY OF THE INVENTION

In accordance with the objects of the invention, there is disclosed, in combination, a medical supplies container comprising a base wall, four upright side walls and a peripheral flange projecting outwardly from the top edges of said side walls, said flange having at least one first bore, and a hypodermic syringe member having a rigid body part, a needle and a needle holder freely engageable in and disengageable from said bore; said bore defining a boring axis and being of such a shape that, when said syringe member needle holder is engaged thereinto and upon its said rigid body part being biased slightly transversely of said boring axis, any pulling of said rigid body part allows egress of said syringe member and associated needle exclusively of said needle holder, wherein the holder can be removed from the syringe needle singlehandedly without having to grasp the holder, the latter remaining into said bore; after use, the syringe needle can be singlehandedly reinserted into its holder without having to manually support the latter, thus preventing contamination by the needle.

Preferably, said syringe member is a trocar, said needle holder being cross-sectionally substantially quadrangular, the trocar extending at right angle to said base wall.

Preferably, said boring axis is perpendicular to the plane defined by said container base wall.

Advantageously, said syringe member is a cannula, said bore merging with the upper portion of the adjacent side wall of said container to constitute a notch or groove, the needle holder seatable flatly into said groove.

Preferably, said groove makes an angle of about 45 degrees with respect to the plane defined by said flange. Also, it is envisioned that said side walls of the container are slightly upwardly outwardly inclined. Moreover, there is profitably further included a small upwardly inwardly offset section of said container base wall at at least one corner portion thereof, for seating another needle holder in substantially upright position wherein the top end portion thereof freely abuts against the corresponding upper end corner portion.

Preferably there is further included a second bore made in the container side wall is register with said first bore, said first and second bores defining a common boring axis, said needle holder being freely engageable/disengageable into said first and second registering bores but frictionally releasably lockable thereinto upon biasing said syringe member rigid body part slightly transversely of these two bores common boring axis. Also, the boring axis passing through said first and second bores advantageously makes an angle of about 30 degrees with respect to said flange, wherein said first and second bores taper thicknesswise.

BRIEF DESCRIPTION OF THE DRAWINGS

FIG. 1 is a perspective view of a medical supplies container in accordance with the teachings of the invention, showing how four differently shaped hypodermic syringes can be safely engaged in or disengaged from their needle tubular holders, the latter engaged in bores made in the container walls, some syringes being shown only in partial view;

FIG. 2 is a sectional view taken along line 2—2 of FIG. 1, but with one syringe being secured to the container in a first connecting fashion;

FIG. 3 is an enlarged top plan view of one corner section of the container;

FIG. 4 is a sectional view taken along line 4—4 of FIG. 3, suggesting how the tubular holder (in dotted lines) of a syringe can be freely positioned into the container of the invention;

FIG. 5 is a sectional view similar to that of FIG. 2, but showing a butterfly syringe needle being secured to the container in a second connecting fashion; and FIG. 6 is a sectional view similar to that of FIG. 2, but showing another type of hypodermic syringe being secured to the container in a third connecting fashion.

DETAILED DESCRIPTION OF THE INVENTION

In FIG. 1, there is shown the medical supplies container of the invention, denoted 10. Container 10 defines a base wall 12, two opposite side walls 14, 16, a front wall 18, a rear wall 20, and a peripheral flange 22 projecting outwardly from the top edges of walls 14 to 20. Walls 14 to 20 are slightly upwardly outwardly divergent, while flange 22 defines a plane parallel to that of said base wall 12. Base wall 12 has a sufficiently large surface area to accommodate a number of medical supplies, such as medical fluid vials (xylocaine, sterile water, etc.), medical instruments (scalpels, forceps, etc.), suture threads, surgical wads, and the l ike.

The front and rear sections of the flange 22, designated 22a, 22b, are about twice as wide as the side sections thereof. Each section 22a, 22b includes any one of number of bores 24, 25, 26, 28; and the front and rear walls 18, 20 each includes a few bores 30, 32, 34, in respective register with bores 24, 26, 28. Each pair of registering bores 24 and 30, 26 and 32, and 28 and 34, are designed to be engaged by corresponding needle holders 40; while each bore 25 is designed to be engaged by another type of needle holder 38. Bores 24, 26 and 28 are similarly shaped, except that they have different dimensions; correspondingly, bores 30, 32, and 34 are similarly shaped, except that they have different dimensions.

A small notch 36 is also made at the intersection of front flange section 22a and front wall 20, so as to define a "groove", designed to accommodate a third type of needle holder 42.

Moreover, it is envisioned that at one or more corner sections of the base wall or flooring 12, there is provided a small inwardly upwardly inclined flooring offset section 44, which appears of triangular shape in top plan view as shown in FIG. 3. Small section 44 is also designed to support a fourth type of needle holder 46, which in this case would not engage into a registering set of bores in walls 14–20 or flange 22.

On a day to day basis, when a nurse wishes to carry medical supplies in the container 10 from the pharmacy to a patient's room, it is recommended that she follows the following loading steps:

(a) add the medical supplies which are to be put directly on the flooring 12 of the container: e.g., the surgical wads, the vials, the forceps, etc.;

(b) add a (non-hypodermic) human ducts probe 48 (if needed), on the flooring 12, to be used by a physician or surgeon, the probe conventionally having a short needle 50 protected by the needle holder 46;

(c) add a hypodermic trocar, hypodermic, syringe, and/or hypodermic cannula, respectively 52, 54 and 56, on the flooring 12.

When the nurse is in the patient's room, she puts the container 10 on a table, an operatively positions the syringes on the container flanges 22a, 22b. This is done by inserting their corresponding needle holders 38, 40 and 42 (which shield their elongated needles 58, 60 and 62) into said bore 25, said bores 24 or 26 or 28 registering with said bores 30 or 32 or 34 respectively, and/or said notch groove 36.

As suggested in FIG. 1, when needle holder 38 engages into its bore 25 or when needle holder 46 seats against its corresponding flooring offset section 44, the respective syringes 52, 48 are substantially upright; whereas when needle holder 40 engages one of the pair of registering bores 24 and 30, 26 and 32, or 28 and 34, the trocar 52 is inclined by about 30 degrees of angle relative to the flooring 12; and when needle holder 42 engages notch groove 36, the cannula 56 is also inclined, by about 45 degrees of angle relative to the flooring 12.

When injection of medicinal fluids or the withdrawal of bodily fluids (especially blood) is deemed necessary by the physician, the nurse may pull out the syringe 54, cannula 56 or trocar 52 from the container 10, by gripping the barrel 52a, 54a thereof (or in the case of the cannula, by gripping the rigid butterfly pad 56a thereof). In accordance with the heart of the invention, while pulling the syringe, cannula or trocar, the nurse, thanks to a method outlined below, will be able to singlehandedly release the corresponding needle 60, 58 or 62 from its needle holder 40, 38 or 42. That is to say, the nurse will not have to grip the needle holder, since the hand of the nurse will always remain clear of the needle. Hence, the possibility that the nurse may accidentally hurt herself with the needle is practically nil.

As for withdrawal of the probe 48 from needle holder 46 and the following reinsertion thereof, the nurse will have to use both hands, one for gripping the holder and the other for gripping the barrel of the probe 48; in view of the stated main object of the invention, since the probe is non-hypodermic by definition, it will not come in contact with blood and therefore there is no danger of AIDS contamination.

Bores 24 to 34 are shaped in accordance with the shape of the corresponding needle holder. For needle holder 40 (which is of cylindrical shape and has exterior longitudinal knurlings) and bores 24 and 26–34, each bore 24, 26 or 28 defines a boring axis which is at about 30 degrees of angle relative to the plane defined by flange sections 22a, 22b. In other words, as clearly shown in FIG. 3, the exterior arcuate edge section of each bore 24, 26 and 28 forms an upwardly outwardly inclined bevel, and the interior arcuate edge section of same bores form a downwardly inwardly inclined bevel. Similarly, each bore 30, 32 or 34 defines a boring axis which is at about 30 degrees of angle relative to a plane perpendicular to the plane defined by flange sections 22a, 22b; and thus, the top arcuate edge section of each of these latter three bores forms an upwardly exteriorly inclined bevel, and similarly, the bottom arcuate edge section thereof forms a downwardly inwardly inclined bevel. Since container walls 14–20 are slightly outwardly upwardly inclined (say by about 10 degrees of angle), the boring axes of the registering bores are not coaxial. The governing principle is that needle holder 40 is freely engageable/disengageable into bores 24, 26, 28, 30, 32, 34; but if the nurse biases with one hand only the barrel 54a of the corresponding syringe 54 slightly upwardly inwardly when pulling same from the container, the needle holder 40 will be temporarily locked into the pair of registering bores into which it is engaged.

Thus, because of the shape of these bores 24 and 26–34, a releasable locking means is defined in this fashion.

Similarly, bore 25 is quadrangular in shape, to conform to the shape of the needle holder 38 which forms a substantially cross-sectional open square. Again, by biasing the barrel trocar 52 transversely to the boring axis of bore 25, the nurse will be able to singlehandedly lock temporarily releasably the holder 38 in its bore 25 while pulling the trocar 52 therefrom.

With respect to notch 36, there is defined a straight channel or groove for engagement by the cylindrical needle holder 42 of the cannula 56. Groove 36 is inversely V-shaped in side view, and substantially U-shaped in end view. By biasing the butterfly pad 56a laterally (i.e. toward one of side walls 14), the nurse will be able to lock temporarily releasably the holder 52 into the groove 36 while pulling the cannula therefrom.

As for holder 46, it is cylindrical in shape and has an enlarged bottom head 46a which may seat against the offset flooring section 44, wherein the top end portion of the holder 46 may freely abut against the upper portion of the merging wall sections of the corresponding walls 14 and 18 (or 20).

After blood has been withdrawn from a patient with a syringe and poured into a testing vial, the syringe is singlehandedly reengaged in its needle holder, which still remains into its bore or channel or registering pair of bores. Thus, the nurse need not manually hold the holder, and there is no danger of contamination with the blood of the patient since the hands of the nurse are away from the path of travel of the needle. When the needle is completely inserted into its holder, the well known "snap action" between the diametrally enlarged inner end sleeve of the needle frictionally locks the needle into its holder. Hence, simply pulling the syringe axially of the container flange boring axis brings therewith the needle holder without having to manually pull the latter therewith.

Of course, a variety of other embodiments of the invention are envisioned to be well within the scope thereof. For instance, bores 24, 25, 26 and 28 could be installed on the side sections of flange 22 instead of the front and rear sections thereof, or even on the four sides thereof, provided these side sections of the flange are sufficiently large to accommodate same. However, the front and rear sections of flange 22 are preferred for these bores, since there must be an area of the container 10 which is free from medical supplies/syringes, for the handling thereof by the nurse. Also, bores 24, 26, 28, 32, 34 could have an irregular shape, such as a knurled shape or being provided with teeth, to improve said frictional locking of the holders 40 when the latter are engaged thereinto.

I claim:

1. In combination, a medical supplies container comprising a base wall, four upright side walls and a peripheral flange projecting outwardly from the top edges of said side walls, said flange having at least one first bore, and a hypodermic syringe member having a rigid body part, a needle and a needle holder freely engageable in and disengageable from said bore; said bore defining a boring axis and being of such a shape that, when said syringe member needle holder is engaged thereinto and upon its said rigid body part being biased slightly transversely of said boring axis, any pulling of said rigid body part allows egress of said syringe member and associated needle exclusively of said needle holder, wherein the holder can be removed from the syringe needle singlehandedly without having to grasp the holder, the latter remaining into said bore; after use, the syringe needle can be singlehandedly reinserted into its holder without having to manually support the latter, thus preventing contamination by the needle.

2. A medical supplies container as defined in claim 1, wherein said syringe member is a trocar, said needle holder being cross-sectionally substantially quadrangular, the trocar extending at right angle to said base wall, said bore being of square shape.

3. A medical supplies container as defined in claim 2, wherein said boring axis is perpendicular to the plane defined by said container base wall.

4. A medical supplies container as defined in claim 1, wherein said syringe member is a cannula, said bore merging with the upper portion of the adjacent side wall of said container to constitute a notch or groove, the needle holder seatable flatly into said groove.

5. A medical supplies container as defined in claim 4, wherein said groove makes an angle of about 45 degrees with respect to the plane defined by said flange.

6. A medical supplies container as defined in claim 1, wherein said side walls of the container are slightly upwardly outwardly inclined.

7. A medical supplies container as defined in claim 1, further including a small upwardly inwardly offset section of said container base wall at at least one corner portion thereof, for seating another needle holder in substantially upright position wherein the top end portion thereof freely abuts against the corresponding upper end corner portion.

8. A medical supplies container as defined in claim 1, further including a second bore made in the container side wall in register with said first bore, said first and second bores defining a common boring axis, said needle holder being freely engageable/disengageable into said first and second registering bores but frictionally releasably lockable thereinto upon biasing said syringe member rigid body part slightly transversely of these two bores common boring axis.

9. A medical supplies container as defined in claim 8, wherein the boring axis passing through said first and second bores makes an angle of about 30 degrees with respect to said flange, wherein said first and second bores taper thicknesswise.

10. A medical supplies container as defined in claim 6, further including a second bore made in the container side wall in register with said first bore, said first and second bores defining a common boring axis, said needle holder being freely engageable/disengageable into said first and second registering bores but frictionally releasably lockable thereinto upon biasing said syringe member rigid body part slightly transversely of these two bores common boring axis.

11. A medical supplies container as defined in claim 10, wherein the boring axis passing through said first and second bores makes an angle of about 30 degrees with respect to said flange, wherein said first and second bores taper thicknesswise.

* * * * *